US010258467B2

United States Patent
Hou et al.

(10) Patent No.: US 10,258,467 B2
(45) Date of Patent: Apr. 16, 2019

(54) MEDICAL GUIDEWIRE

(71) Applicant: BOSTON SCIENTIFIC SCIMED, INC., Maple Grove, MN (US)

(72) Inventors: Dongming Hou, Plymouth, MN (US); John Jianhua Chen, Plymouth, MN (US); Robert Chang, Belmont, CA (US); Takashi H. Ino, San Jose, CA (US); Benjamin T. Sutton, Scotts Valley, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 154 days.

(21) Appl. No.: 15/389,224

(22) Filed: Dec. 22, 2016

(65) Prior Publication Data

US 2017/0100244 A1  Apr. 13, 2017

Related U.S. Application Data

(63) Continuation of application No. 14/458,757, filed on Aug. 13, 2014.

(Continued)

(51) Int. Cl.
*A61F 2/24* (2006.01)
*A61M 25/09* (2006.01)

(52) U.S. Cl.
CPC ........... *A61F 2/2427* (2013.01); *A61M 25/09* (2013.01); *A61M 25/0905* (2013.01);
(Continued)

(58) Field of Classification Search
CPC . A61F 2/2427; A61M 25/09; A61M 25/0905; A61M 2025/09008;
(Continued)

(56) References Cited

U.S. PATENT DOCUMENTS 4,576,142 A * 3/1986 Schiff ................. A61M 1/1072
600/18
4,971,490 A   11/1990 Hawkins
(Continued)

FOREIGN PATENT DOCUMENTS

WO        9221282 A1    12/1992
WO     1997018006 A1     5/1997
(Continued)

OTHER PUBLICATIONS

Harrison et al, Gareth, "Guidewire Stiffness: What's in a Name?" International Society of Endovascular Specialists, 2011.
(Continued)

*Primary Examiner* — Jocelin C Tanner
(74) *Attorney, Agent, or Firm* — Seager, Tufte & Wickhem LLP.

(57) ABSTRACT

A guidewire system may include a guidewire having a relatively stiff proximal section and a relatively flexible distal section joined by a transition region, and a TAVI device slidably disposed on the guidewire. The guidewire may include an expandable element disposed about the transition region. The expandable element may be configured to expand from a collapsed configuration to an expanded configuration. The guidewire may include an expandable element disposed at the distal end. The distal section may be pre-configured to form more than one distal loop. A method of protecting an apex of a left ventricle during a TAVI procedure may include inserting a guidewire into the left ventricle, positioning a transition region adjacent the apex, expanding an expandable element such that the expandable element spans the apex, advancing a TAVI device distally over the guidewire to an aortic valve, and performing a TAVI procedure at the aortic valve.

16 Claims, 17 Drawing Sheets

Related U.S. Application Data

(60) Provisional application No. 61/865,800, filed on Aug. 14, 2013.

(52) U.S. Cl.
CPC .............. *A61M 2025/091* (2013.01); *A61M 2025/09008* (2013.01); *A61M 2025/0915* (2013.01); *A61M 2025/09133* (2013.01); *A61M 2025/09166* (2013.01); *A61M 2025/09175* (2013.01); *A61M 2025/09183* (2013.01); *A61M 2210/125* (2013.01); *A61M 2210/127* (2013.01)

(58) Field of Classification Search
CPC ........... A61M 2025/09133; A61M 2025/0915; A61M 2025/09166; A61M 2025/09175; A61M 2025/09183; A61M 2210/125; A61M 2210/127
See application file for complete search history.

(56) References Cited

U.S. PATENT DOCUMENTS

| | | | |
|---|---|---|---|
| 5,772,609 A | | 6/1998 | Nguyen et al. |
| 5,908,405 A | | 6/1999 | Imran et al. |
| 6,132,389 A | * | 10/2000 | Cornish ................ A61M 25/09 600/585 |
| 6,139,510 A | | 10/2000 | Palermo |
| 6,595,989 B1 | | 7/2003 | Schaer |
| 6,918,882 B2 | | 7/2005 | Skujins et al. |
| 7,393,360 B2 | | 7/2008 | Spenser et al. |
| 8,182,530 B2 | | 5/2012 | Huber |
| 2002/0156526 A1 | * | 10/2002 | Hlavka ................ A61F 2/2445 623/2.11 |
| 2003/0069521 A1 | | 4/2003 | Reynolds et al. |
| 2003/0163156 A1 | | 8/2003 | Hebert et al. |
| 2004/0073141 A1 | * | 4/2004 | Hartley ................ A61M 25/09 600/585 |
| 2004/0142643 A1 | | 7/2004 | Miller et al. |
| 2004/0167441 A1 | | 8/2004 | Reynolds et al. |
| 2004/0260331 A1 | | 12/2004 | D'Aquanni et al. |
| 2008/0097402 A1 | | 4/2008 | Hoganson et al. |
| 2008/0287983 A1 | | 11/2008 | Smith et al. |
| 2009/0054905 A1 | * | 2/2009 | Levy ................ A61B 17/12022 606/108 |
| 2009/0216221 A1 | * | 8/2009 | Davis .................. A61B 18/082 606/33 |
| 2010/0274085 A1 | | 10/2010 | Mugan et al. |
| 2010/0312179 A1 | | 12/2010 | Nikolchev et al. |
| 2011/0021985 A1 | * | 1/2011 | Spargias ................ A61L 29/08 604/96.01 |
| 2011/0213459 A1 | | 9/2011 | Garrison et al. |
| 2012/0209375 A1 | | 8/2012 | Madrid et al. |
| 2013/0046376 A1 | * | 2/2013 | Hassan ................ A61M 25/09 623/2.11 |
| 2013/0046379 A1 | | 2/2013 | Paolitto et al. |
| 2013/0158655 A1 | | 6/2013 | Sutton et al. |
| 2013/0197571 A1 | * | 8/2013 | Hariton .............. A61B 17/0057 606/213 |
| 2013/0261738 A1 | * | 10/2013 | Clague .................. A61F 2/2418 623/2.11 |

FOREIGN PATENT DOCUMENTS

| | | |
|---|---|---|
| WO | 2000060995 A2 | 10/2000 |
| WO | 2003000331 A1 | 1/2003 |
| WO | 2008060529 A2 | 5/2008 |
| WO | 2013128461 A1 | 9/2013 |

OTHER PUBLICATIONS

Rezq et al., "Incidence, Management, and Outcomes of Cardiac Tamponade During Transcatheter Aortic Valve Implantation," JACC: Cardiovascular Interventions, vol. 5(12):1264-1272, Dec. 2012.

\* cited by examiner

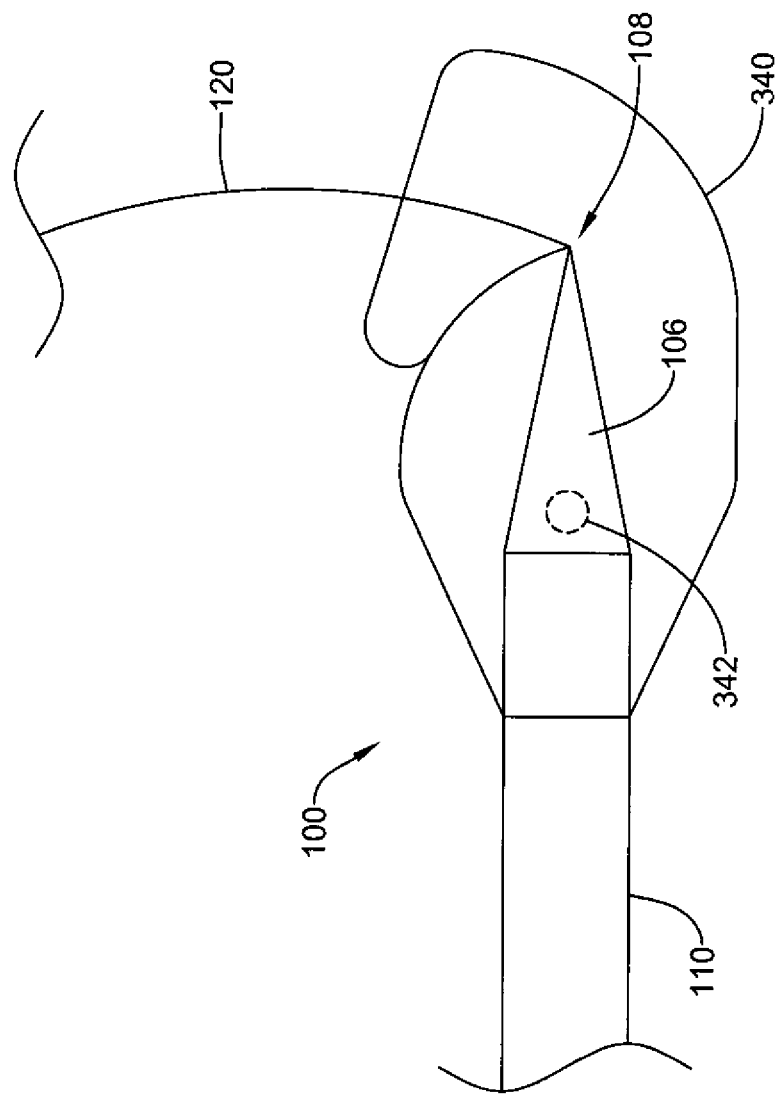

MEDICAL GUIDEWIRE

CROSS-REFERENCE TO RELATED APPLICATIONS

This application is a continuation application of U.S. application Ser. No. 14/458,757, filed Aug. 13, 2014, which is a non-provisional application of U.S. Ser. No. 61/865,800 filed Aug. 14, 2013.

TECHNICAL FIELD

The disclosure relates generally to medical devices and more particularly to medical devices that are adapted for use in procedures for repairing heart valves.

BACKGROUND

Aortic valve stenosis is a frequent expression of valvular heart disease, and may often be a leading indicator for valve replacement therapy in Europe and the United States. The prevalence of aortic valve stenosis tends to increase in older population groups. In some cases, traditional open-heart valve replacement surgery is not suitable for patients with higher surgical risk factors. Alternate therapies, and/or linking therapies that may transition an at-risk patient to a more suitable condition for traditional open-heart valve replacement surgery, may be beneficial in improving the lifestyle of patients suffering from aortic valve stenosis.

A continuing need exists for improved devices and methods for use in alternative or predecessor treatments to traditional open-heart valve replacement surgery.

SUMMARY

A guidewire system may include a guidewire having a proximal end, a distal end, and a length extending therebetween, wherein the guidewire includes a relatively stiff proximal section and a relatively flexible distal section joined by a transition region, and a TAVI device slidably disposed on the guidewire, wherein the guidewire includes an expandable element disposed about the transition region in a first position, wherein the expandable element is configured to expand from a collapsed configuration to an expanded configuration.

A guidewire system may include a guidewire having a proximal end, a distal end, and a length extending therebetween, wherein the guidewire includes a relatively stiff proximal section and a relatively flexible distal section joined by a transition region, and a TAVI device slidably disposed on the guidewire, wherein the guidewire includes an expandable element disposed at the distal end.

A guidewire system may include a guidewire having a proximal end, a distal end, and a length extending therebetween, wherein the guidewire includes a relatively stiff proximal section and a relatively flexible distal section joined by a transition region, and a TAVI device slidably disposed on the guidewire, wherein the distal section is pre-configured to form more than one distal loop.

A method of protecting an apex of a left ventricle of a heart of a patient during a TAVI procedure may include inserting a guidewire upstream through an aorta of the patient and into the left ventricle, the guidewire including a relatively stiff proximal section, a relatively flexible distal section joined to the proximal section by a transition region, and an expandable element disposed about the transition region; positioning the transition region adjacent the apex; expanding the expandable element from a collapsed configuration to an expanded configuration within the left ventricle such that the expandable element spans the apex; advancing a TAVI device distally over the guidewire to an aortic valve; and performing a TAVI procedure at the aortic valve.

Although discussed with specific reference to use within the coronary vasculature of a patient, for example to repair a heart valve, medical devices and methods of use in accordance with the disclosure can be adapted and configured for use in other parts of the anatomy, such as the digestive system, the respiratory system, or other parts of the anatomy of a patient.

BRIEF DESCRIPTION OF THE FIGURES

FIG. 8 is a side view of an example guidewire system;

Figure 1:
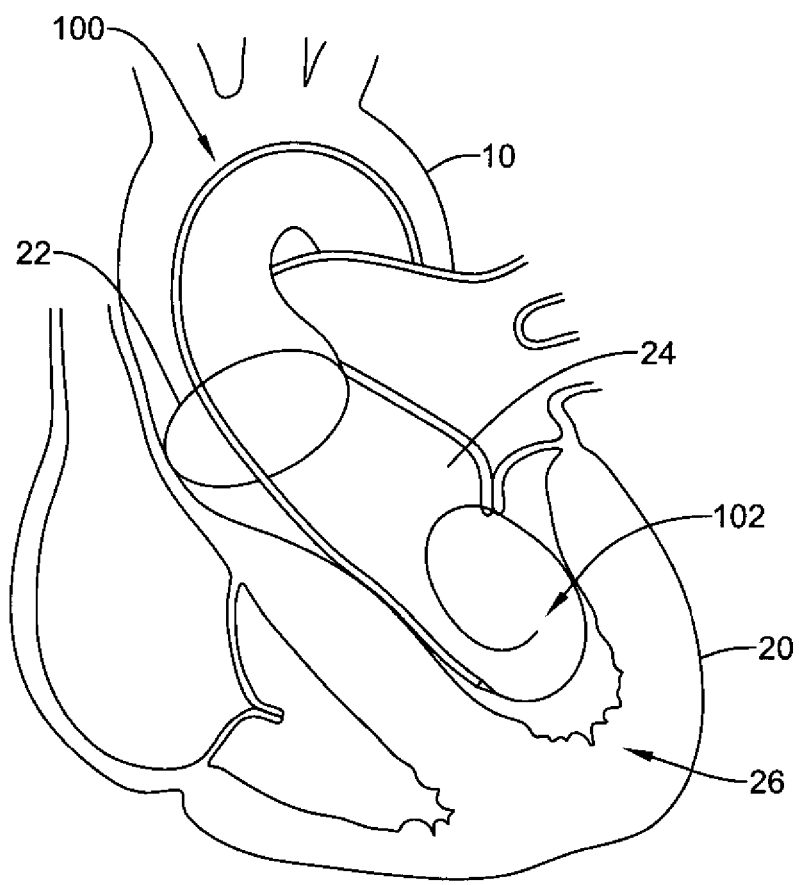
FIG. 1 is a schematic partial view of an aortic heart valve having an example guidewire system disposed therein.

While the invention is amenable to various modifications and alternative forms, specifics thereof have been shown by way of example in the drawings and will be described in greater detail below. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. One of ordinary skill in the art will readily appreciate and understand that a particular element or feature from any disclosed or illustrated example embodiment herein may be incorporated into any other example embodiment unless expressly stated otherwise. The detailed description and drawings are intended to illustrate but not limit the claimed invention.

For the following defined terms, these definitions shall be applied, unless a different definition is given in the claims or elsewhere in this specification.

The terms "upstream" and "downstream" refer to a position or location relative to the direction of blood flow through a particular element or location, such as a vessel (i.e., the aorta), a heart valve (i.e., the aortic valve), and the like.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to a serious health condition and/or death if not dealt with. A human heart includes several different heart valves, including aortic, pulmonary, mitral, and tricuspid valves, which control the flow of blood to and from the heart. Over time, a heart valve may become obstructed, narrowed, and/or less flexible (i.e., stenosed) due to hardening, calcium deposition, or other factors, thereby reducing the flow of blood through the valve and/or increasing the pressure within the chambers of the heart as the heart attempts to pump the blood through the vasculature. One traditional treatment method is valve replacement, where the stenosed valve is removed and a replacement tissue or mechanical valve is implanted via open heart surgery. Alternative treatments, including percutaneous valve replacement procedures (i.e., transcatheter aortic valve implantation, or TAVI) which may deliver and implant a replacement heart valve (i.e., aortic valve), have been developed which may be much less invasive to the patient. The devices and methods described herein may provide additional desirable features and benefits for use in such procedures.

A typical aortic valve may comprise three leaflets, although two leaflet and four leaflet valves are known to occur in a portion of the population. For simplicity, the following discussion will be described in the context of treating a typical aortic valve. However, it is fully contemplated that the devices and methods described herein may be adapted for use in the treatment of a two or four (or more) leaflet heart valve and/or a non-aortic heart valve. One of ordinary skill in the art will understand that in the event of treating a non-aortic heart valve, the relative orientations and directions associated with the described devices and methods may be modified to accommodate the specifics (i.e., orientation, location, size, etc.) of the heart valve undergoing treatment.

FIG. 1 schematically illustrates a guidewire 100 disposed within an aorta 10, and/or an aortic valve 22 and a left ventricle 24 of a heart 20. Treatment of an aortic valve 22 using a TAVI device may sometimes involve insertion of a relatively stiff guidewire 100, which may or may not have a relatively flexible distal tip, upstream through the aorta 10 and/or the aortic valve 22 into the left ventricle 24. Later, a suitable TAVI device may be inserted and/or advanced over the guidewire 100 to the heart 20 and/or the aortic valve 22. As shown in FIG. 1, the guidewire 100 may extend upstream through the aorta 10, across or through the aortic arch, and through the aortic valve 22 into the left ventricle 24 of a patient's heart 20. In some embodiments, a distal end 102 of the guidewire 100 may be positioned within the left ventricle 24 during a TAVI procedure.

In some embodiments, the guidewire 100 may have a substantially solid cross-section. In some embodiments, the guidewire 100 may be tubular or hollow in construction, with one or more lumens disposed therein, such as, for example, a hypotube or a thin-walled tubular catheter. Those of skill in the art and others will recognize that the materials, structures, and dimensions of the guidewire 100 are dictated primarily by the desired characteristics and function of the final guidewire, and that any of a broad range of materials, structures, and dimensions can be used.

For example, the guidewire 100 may be formed of any materials suitable for use, dependent upon the desired properties of the guidewire 100. Some examples of suitable materials include metals, metal alloys, polymers, composites, or the like, or combinations or mixtures thereof. Some examples of suitable metals and metal alloys include stainless steel, such as 304V, 304L, and 316L stainless steel; alloys including nickel-titanium alloy such as linear elastic or superelastic (i.e., pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. In some embodiments, it is desirable to use metals or metal alloys that are suitable for metal joining techniques such as welding, soldering, brazing, crimping, friction fitting, adhesive bonding, etc. The particular material used can also be chosen in part based on the desired flexibility requirements or other desired characteristics.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Within the family of commercially available nitinol alloys is a category designated "linear elastic" which, although similar in chemistry to conventional shape memory and superelastic (i.e., pseudoelastic) varieties, exhibits distinct and useful mechanical properties. By skilled applications of cold work, directional stress and heat treatment, the wire is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range.

For example, in some embodiments, there are no martensite/austenite phase changes detectable by DSC and DMTA analysis in the range of about −60° C. to about 120° C. The mechanical bending properties of such a material are therefore generally inert to the effect of temperature over this very broad range of temperatures. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy.

In some embodiments, the linear elastic nickel-titanium alloy is in the range of about 50 to about 60 weight percent nickel, with the remainder being essentially titanium. In some particular embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of suitable nickel-titanium alloys include those disclosed in U.S. Pat. Nos. 5,238,004 and 6,508,803, which are incorporated herein by reference. In some other embodiments, a superelastic alloy, for example a superelastic nitinol, can be used to achieve desired properties.

Portions or all of the guidewire 100, or other structures (i.e., markers, for example) included within the guidewire 100, may in some cases be doped with, coated or plated with, made of, or otherwise include a radiopaque material. Radiopaque materials are understood to be materials capable of producing a relatively bright image on a fluoroscopy screen or another imaging technique during a medical procedure. This relatively bright image aids the user of the guidewire 100 in determining its location. Some examples of radiopaque materials can include, but are not limited to, gold, platinum, palladium, tantalum, tungsten alloy, polymer material loaded with a radiopaque filler, and the like, or combinations or alloys thereof.

Additionally, in some instances a degree of MRI compatibility can be imparted into the guidewire 100. For example, to enhance compatibility with Magnetic Resonance Imaging (MRI) machines, the guidewire 100, or other portions of the guidewire 100, can be made in a manner that would impart a degree of MRI compatibility. For example, the guidewire 100, or portions thereof, may be made of a material that does not substantially distort the image and create substantial artifacts (artifacts are gaps in the image) during MRI imaging. Certain ferromagnetic materials, for example, may not be suitable because they may create artifacts in an MRI image. The guidewire 100, or portions thereof, may also be made from a material that the MRI machine can image. Some materials that exhibit these characteristics include, for example, tungsten, Elgiloy™, MP35N, nitinol, and the like, and others, or combinations or alloys thereof.

A particular cross-sectional shape of the guidewire 100 can be any desired shape, for example rounded, oval, rectangular, square, polygonal, and the like, or other such various cross-sectional geometries. The cross-sectional geometries along the length of the guidewire 100 can be constant or can vary. For example, the figures depict the guidewire 100 as having a generally constant round cross-sectional shape, but it can be appreciated that other cross-sectional shapes or combinations of shapes, while not expressly illustrated, may be utilized without departing from the spirit of the invention.

Figure 2:
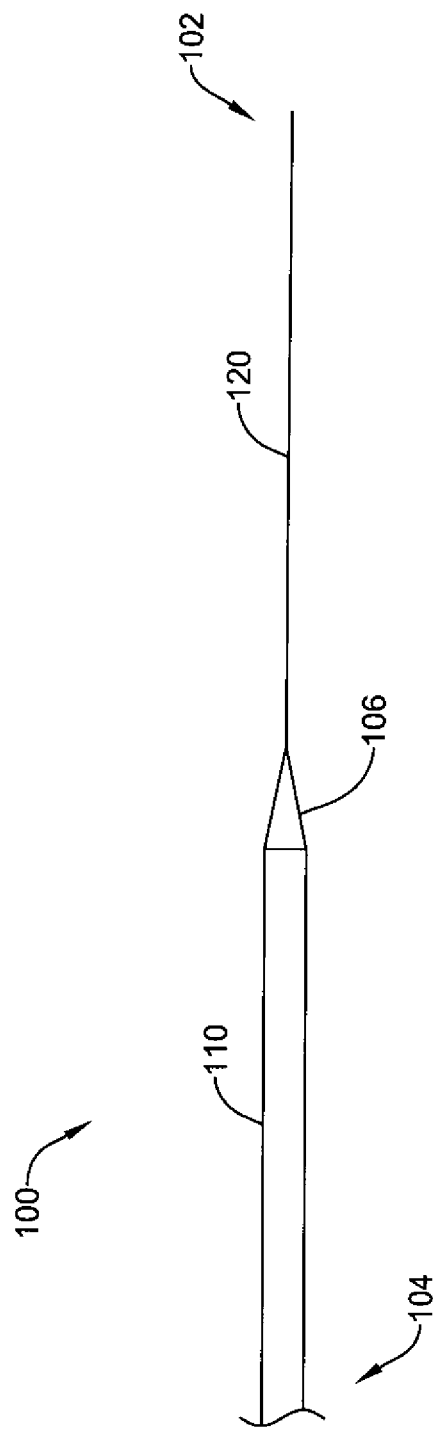
FIG. 2 is a side view of an example guidewire system.

The guidewire 100 may include a distal end 102 and a proximal end 104, as illustrated for example, in FIG. 2. In some embodiments, the guidewire 100 may include a transition region 106 disposed between the proximal end 104 and the distal end 102, the transition region 106 providing a transition in stiffness/flexibility characteristics of the guidewire 100 along the length thereof. In some embodiments, the guidewire 100 may include one or more tapers and/or tapered regions, one or more constant diameter sections, and/or may generally include a constant inner and outer diameter. The tapers and/or constant diameters may be manifested in variations and/or consistencies in the size of the outer diameter, inner diameter, and/or wall thickness of the guidewire 100. The constant diameter sections may be the same diameter or different diameters. For example, as illustrated in FIG. 2, a proximal section 110 may have a first generally constant diameter and a distal section 120 may have a second generally constant diameter. In some embodiments, the second diameter may be less than the first diameter. In some embodiments, the first diameter may be less than the second diameter. In some embodiments, the first diameter and the second diameter may be substantially equal. In some embodiments, the proximal section 110 and/or the distal section 120 may be tapered and/or have a varying diameter.

In some embodiments, a tapered transition region 106 may be disposed between the proximal section 110 and the distal section 120, as seen in FIG. 2. In some embodiments, the tapered transition region 106 may taper distally from the first diameter to the second diameter. Tapered transition region(s) 106 may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness/flexibility characteristics. It can be appreciated that essentially any portion of the guidewire 100 may be tapered or can have a constant diameter, and that any tapers and/or constant diameter can extend in either the proximal or the distal direction, for example, to achieve the desired flexibility, stiffness, and/or torque transmission characteristics.

In some embodiments, the guidewire 100 may have one or more lumens having an inner diameter that is in the range of about 0.008 inch to about 0.030 inch in size, and in some embodiments, in the range of about 0.015 inch to about 0.025 inch in size. Additionally, in some embodiments, the guidewire 100 may have a maximum or first outer diameter that is in the range of about 0.010 inch to about 0.050 inch in size, and in some embodiments, in the range of about 0.020 inch to about 0.040 inch in size, and in some embodiments, about 0.035 inch. It should be understood however, that these and other dimensions provided herein are by way of example embodiments only, and that in other embodiments, the size of the inner and outer diameter of the guidewire 100 can vary greatly from the dimensions given, depending upon the desired characteristics and function of the device.

An outer profile of the guidewire 100, including any tapered and/or constant diameter portions, may be formed by any one of a number of different techniques, for example, by centerless grinding methods, stamping methods, extrusion methods, co-extrusion methods, and the like. A centerless grinding technique may utilize an indexing system employing sensors (e.g., optical/reflective, magnetic) to avoid excessive grinding. In addition, the centerless grinding technique may utilize a CBN or diamond abrasive grinding wheel that is well shaped and dressed to avoid grabbing the guidewire 100 during the grinding process. In some embodiments, centerless grinding can be achieved using a Royal Master HI-AC centerless grinder. Some examples of suitable grinding methods are disclosed in U.S. patent application Ser. No. 10/346,698 filed Jan. 17, 2003 (Pub. No. U.S. 2004/0142643), which is herein incorporated by reference.

The guidewire 100 may also include structure or otherwise be adapted and/or configured to achieve a desired level of stiffness, torqueability, flexibility, and/or other characteristics. The desired stiffness, torqueability, lateral flexibility, bendability or other such characteristics of the guidewire 100 can be imparted, enhanced, or modified by the particular structure that may be used or incorporated into the guidewire 100. As can thus be appreciated, the flexibility of the guidewire 100 can vary along its length, for example, such that the flexibility can be higher at the distal end 102 relative to the proximal end 104, or vice versa. In some embodiments, the distal section 120 may be more flexible than the proximal section 110. However, in some embodiments, the guidewire 100 can have a substantially constant flexibility along the entire length thereof. In some embodiments, the distal section 120 may be pre-shaped to form a distal loop disposed distally of the tapered region 106 within the distal section 120.

One manner of imparting additional flexibility is to selectively remove material from portions of the guidewire. For example, a guidewire may include a thin wall tubular structure including a plurality of apertures, such as grooves, cuts, slits, slots, or the like, formed in a portion of, or along the entire length of, the guidewire. The plurality of apertures may be formed such that one or more spines or beams are formed in the guidewire. Such spines or beams could include portions of the guidewire that remain after the plurality of apertures is formed in the thin wall tubular structure of the guidewire, and may act to maintain a relatively high degree of torsional stiffness while maintaining a desired level of lateral flexibility due to the plurality of apertures. Such structure may be desirable because it may allow guidewire, or portions thereof, to have a desired level of laterally flexibility as well as have the ability to transmit torque and pushing forces from the proximal end to the distal end. The plurality of apertures can be formed in essentially any known way. For example, the plurality of apertures can be formed by methods such as micro-machining, saw-cutting, laser cutting, grinding, milling, casting, molding, chemically etching or treating, or other known methods, and the like. In some such embodiments, the structure of the guidewire is formed by cutting and/or removing portions of the thin wall tubular structure to form the plurality of apertures.

In some embodiments, the plurality of apertures can completely penetrate an outer wall of the guidewire such that there is fluid communication between a lumen extending therethrough (i.e., defined by the outer wall) and an exterior of the guidewire through the plurality of apertures. The shape and size of the plurality of apertures can vary, for example, to achieve the desired characteristics. For example, the shape of the plurality of apertures can vary to include essentially any appropriate shape, such as squared, round, rectangular, pill-shaped, oval, polygonal, elongated, irregular, spiral (which may or may not vary in pitch), or other suitable means or the like, and may include rounded or squared edges, and can be variable in length and width, and the like. In some embodiments, a guidewire may include a helical coil having adjacent turns spaced apart to form a plurality of apertures extending through to an interior lumen. Other configurations, arrangements, and/or combinations thereof may also be used.

In some embodiments, some adjacent apertures can be formed such that they include portions that overlap with each other about the circumference of the guidewire. In other embodiments, some adjacent apertures can be disposed such that they do not necessarily overlap with each other, but are disposed in a pattern that provides the desired degree of lateral flexibility. Additionally, the apertures can be arranged along the length of, or about the circumference of, the guidewire to achieve desired properties. For example, the apertures can be arranged in a symmetrical pattern, such as being disposed essentially equally on opposite sides about the circumference of the guidewire, or equally spaced along the length of the guidewire, or can be arranged in an increasing or decreasing density pattern, or can be arranged in a non-symmetric or irregular pattern.

As can be appreciated, the spacing, arrangement, and/or orientation of the plurality of apertures, or in the associated spines or beams that may be formed, can be varied to achieve the desired characteristics. For example, the number, proximity (to one another), density, size, shape, and/or depth of the plurality of apertures along the length of the guidewire may vary in either a stepwise fashion or consistently, depending upon the desired characteristics. For example, the quantity or proximity of the plurality of apertures to one another near one end of the guidewire may be high, while the quantity or proximity of the plurality of apertures to one another near the other end of the guidewire, may be relatively low, or vice versa. For example, in the some embodiments, a distal region of the guidewire may include a greater density of apertures, while a proximal region of the guidewire may include a lesser density of apertures, or may even be devoid of any apertures. As such, the distal region may have a greater degree of lateral flexibility relative to the proximal region. It should be understood that similar variations in the size, shape and/or depth of the plurality of apertures along the length of the guidewire can also be used to achieve desired flexibility differences thereof.

The flexibility characteristics of a guidewire could also be achieved using other methods, such as by the addition of material and/or one or more reinforcement members to certain portions of the guidewire. As understood by one of skill in the art, any of a broad variety of attachment techniques and/or structures can be used to attachment additional material and/or one or more reinforcement members to a guidewire. Some examples of suitable attachment techniques include welding, soldering, brazing, crimping, friction fitting, adhesive bonding, mechanical interlocking and the like.

Some examples of welding processes that can be suitable in some embodiments include LASER welding, resistance welding, TIG welding, microplasma welding, electron beam welding, friction welding, inertia welding, or the like. LASER welding equipment which may be suitable in some applications is commercially available from Unitek Miyachi of Monrovia, Calif. and Rofin-Sinar Incorporated of Plymouth, Mich. Resistance welding equipment which may be suitable in some applications is commercially available from Palomar Products Incorporated of Carlsbad, Calif. and Polaris Electronics of Olathe, Kans. TIG welding equipment which may be suitable in some applications is commercially available from Weldlogic Incorporated of Newbury Park, Calif. Microplasma welding equipment which may be suitable in some applications is commercially available from Process Welding Systems Incorporated of Smyrna, Tenn.

In some embodiments, LASER or plasma welding can be used to achieve the attachment. In LASER welding, a light beam is used to supply the necessary heat. LASER welding can be beneficial in the processes contemplated by the invention, as the use of a LASER light heat source can provide significant accuracy. It should also be understood that such LASER welding can also be used to attach other components to the device. Additionally, in some embodiments, LASER energy can be used as the heat source for soldering, brazing, or the like for attaching different components or structures of the guidewire together. Again, the use of a LASER as a heat source for such connection techniques can be beneficial, as the use of a LASER light heat source can provide substantial accuracy. One particular example of such a technique includes LASER diode soldering.

Additionally, in some other example embodiments, attachment may be achieved and/or aided through the use of a mechanical connector or body, and/or by an expandable alloy, for example, a bismuth alloy. Some examples of methods, techniques and structures that can be used to interconnect different portions of a guidewire using such expandable material are disclosed in a U.S. patent application Ser. No. 10/375,766 filed Feb. 26, 2003 (Pub. No. U.S. 2004/0167441), which is hereby incorporated herein by reference. Some methods and structures that can be used to interconnect different sections are disclosed in U.S. Pat. No. 6,918,882, and U.S. patent application Ser. No. 10/086,992 filed Feb. 28, 2002 (Pub. No. U.S. 2003/0069521), which are incorporated herein by reference.

Additionally, in some embodiments, a coating, for example a lubricious (i.e., hydrophilic, hydrophobic, etc.) or other type of coating may be applied over portions or all of the guidewire 100 discussed above. Hydrophobic coatings such as fluoropolymers, silicones, and the like provide a dry lubricity which improves guidewire handling and device exchanges. Lubricious coatings improve steerability and improve lesion crossing capability. Suitable lubricious polymers are well known in the art and may include (but are not limited to) hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, a more distal portion of a guidewire is coated with a hydrophilic polymer, and a more proximal portion is coated with a fluoropolymer, such as polytetrafluroethylene (PTFE).

The use of a coating layer in some embodiments can impart a desired flexibility to the guidewire. Choice of coating materials may vary, depending upon the desired characteristics. For example, coatings with a low durometer or hardness may have very little effect on the overall flexibility of the guidewire. Conversely, coatings with a high durometer may make for a stiffer and/or less flexible shaft.

Figure 3:
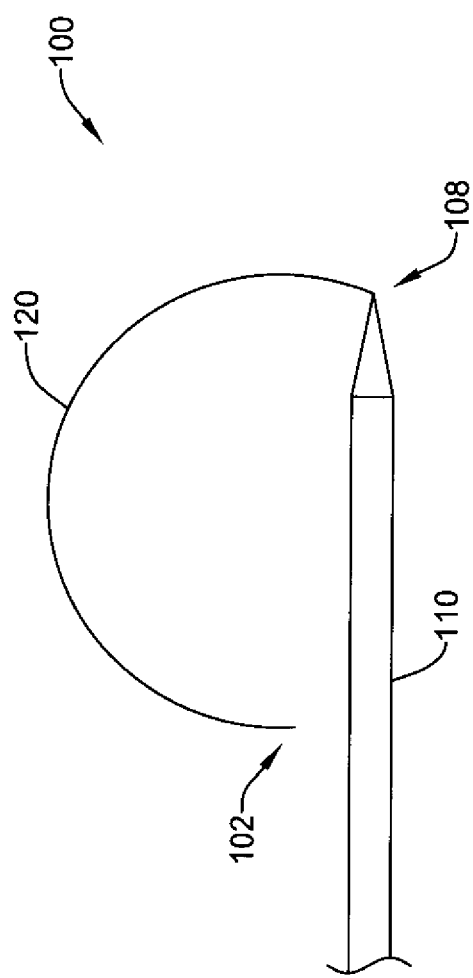
FIG. 3 is a side view of an example guidewire system.

In use, a distal end 102 of the guidewire 100 may be advanced percutaneously upstream within a patient's aorta 10 to a treatment site (i.e., a patient's heart 20 and/or an aortic valve 22). The distal end 102 may be advanced through the treatment site (i.e., the patient's aortic valve 22) into a patient's left ventricle 24. In some embodiments, the distal section 120 may curl within the left ventricle 24 and/or make contact with an apex 26 of the left ventricle, as seen in FIG. 1. In general, the distal section 120 may be flexible enough to bend and/or curl within the left ventricle 24 so as to form a distal loop. However, in some embodiments, the proximal section 110 may be stiffer than the distal section 120 and may resist bending. In some cases, contact within the apex 26 may result in a kink 108 forming within or adjacent to the distal section 120, as illustrated for example, in FIGS. 3 and 4. The kink 108 may undesirably perforate a wall of the left ventricle 24, for example at or near the apex 26.

Figure 5A:
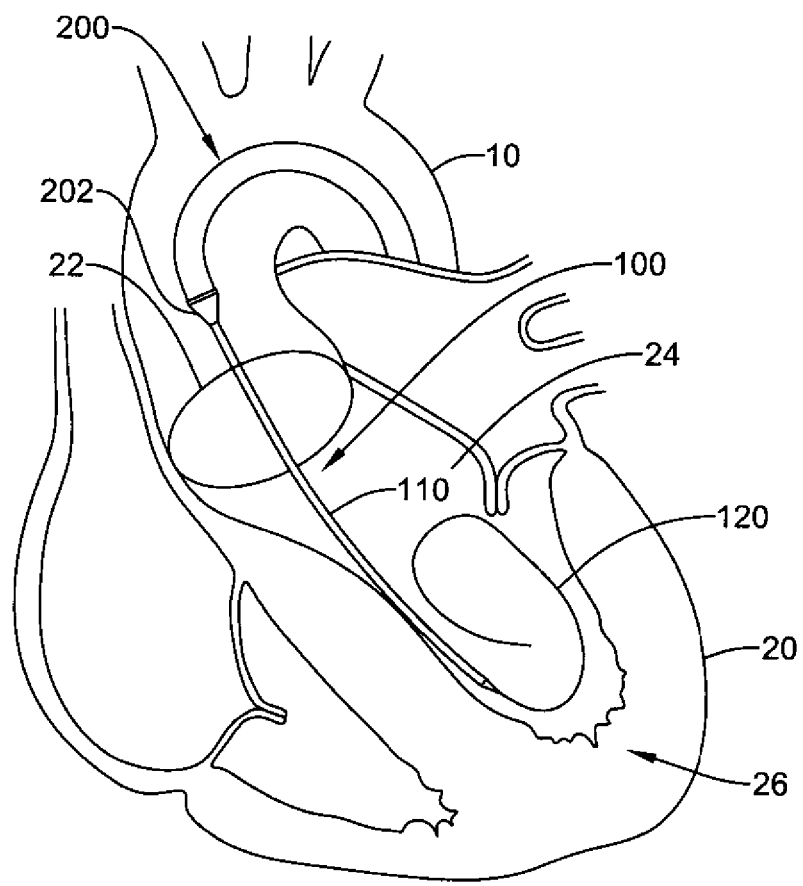
FIG. 5A is a schematic partial view of an example TAVI device disposed on an example guidewire system disposed within an aortic heart valve.
Figure 5B:
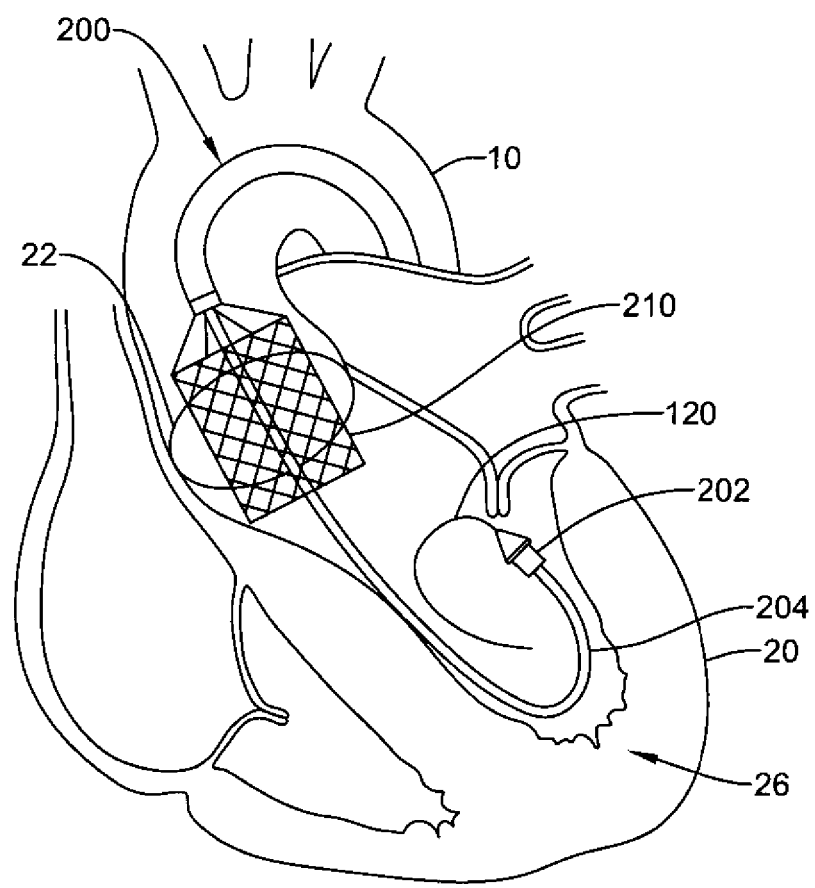
FIG. 5B is a schematic partial view of the example TAVI device of FIG. 5A expanded within the aortic heart valve.

FIG. 5A illustratively shows a typical positioning of the guidewire 100 within the aorta 10 and the left ventricle 24 during a TAVI procedure. A suitable TAVI device 200 may be disposed on and/or advanced distally over the guidewire 100. In some embodiments, the TAVI device 200 may end in a position illustrated in FIG. 5B, wherein a portion of the TAVI device 200 (i.e., nosecone 202, for example, which may be attached to an inner shaft 204 in some embodiments) may follow the guidewire 100 past the apex 26. During use, the nosecone 202 may be advanced far enough into the left ventricle 24 to provide adequate clearance for deployment and/or expansion of a replacement heart valve member. In some embodiments, the TAVI device 200 may end in a position illustrated in FIG. 5B, wherein a portion of the TAVI device 200 (i.e., nosecone 202, for example) may track the guidewire 100 past the apex 26. This may happen, for example, in instances where the patient being treated has a small left ventricle. In some cases, movement of the TAVI device 200 over the guidewire 100 and/or deployment of the replacement heart valve member 210 may result in the stiffer proximal section 110 of the guidewire 100 perforating a wall of the left ventricle 24 due to friction (i.e., a "sawing" effect, for example), excessive pressure placed on the wall of the ventricle 24, abrasion by passage of the nosecone 202, or for other reasons.

Figure 6:
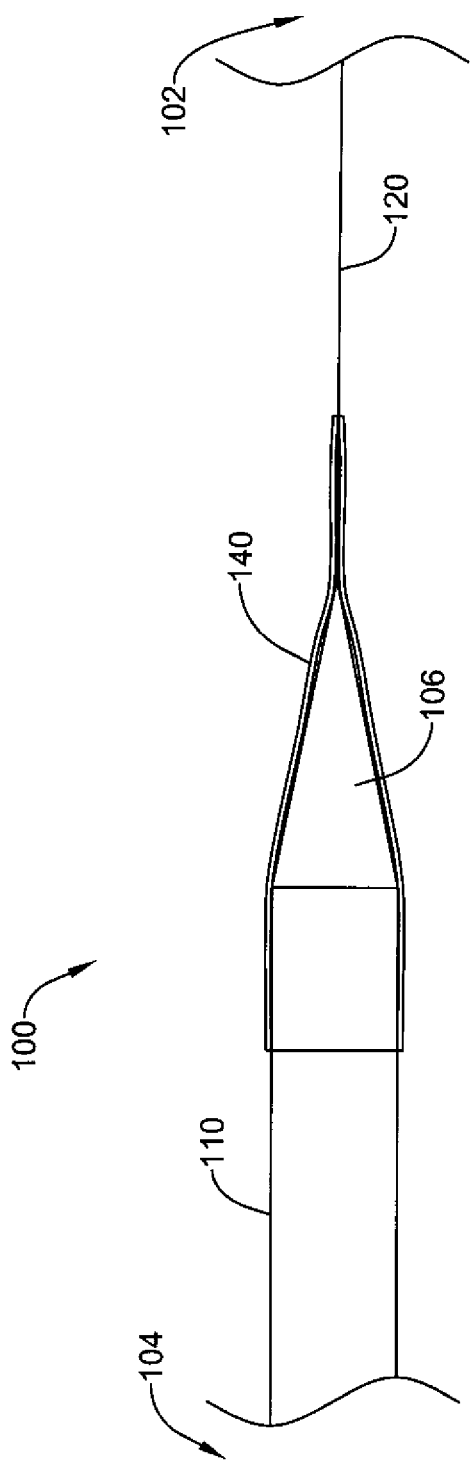
FIG. 6 is a side view of an example guidewire system.

FIG. 6 schematically illustrates an expandable protection element 140 disposed on, over, or about the guidewire 100 in a collapsed configuration. In some embodiments, the expandable protection element 140 may extend from or over at least a portion of the proximal section 110, across the tapered region 106, and onto or over at least a portion of the distal section 120. In some embodiments, the guidewire 100 may extend through the expandable protection element 140. In some embodiments, the expandable protection element 140 may be disposed alongside or adjacent to the guidewire 100. In some embodiments, the expandable protection element 140 may be disposed at a position along a length of the guidewire 100 most likely to form or develop kink 108 and/or to be located at or within the apex 26. In some embodiments, the expandable protection element 140 may be designed and/or configured to be placed within the apex 26. In some embodiments, the expandable protection element 140 may be located within the apex 26 through normal operation of the guidewire 100 and/or the TAVI device 200.

Figure 7:
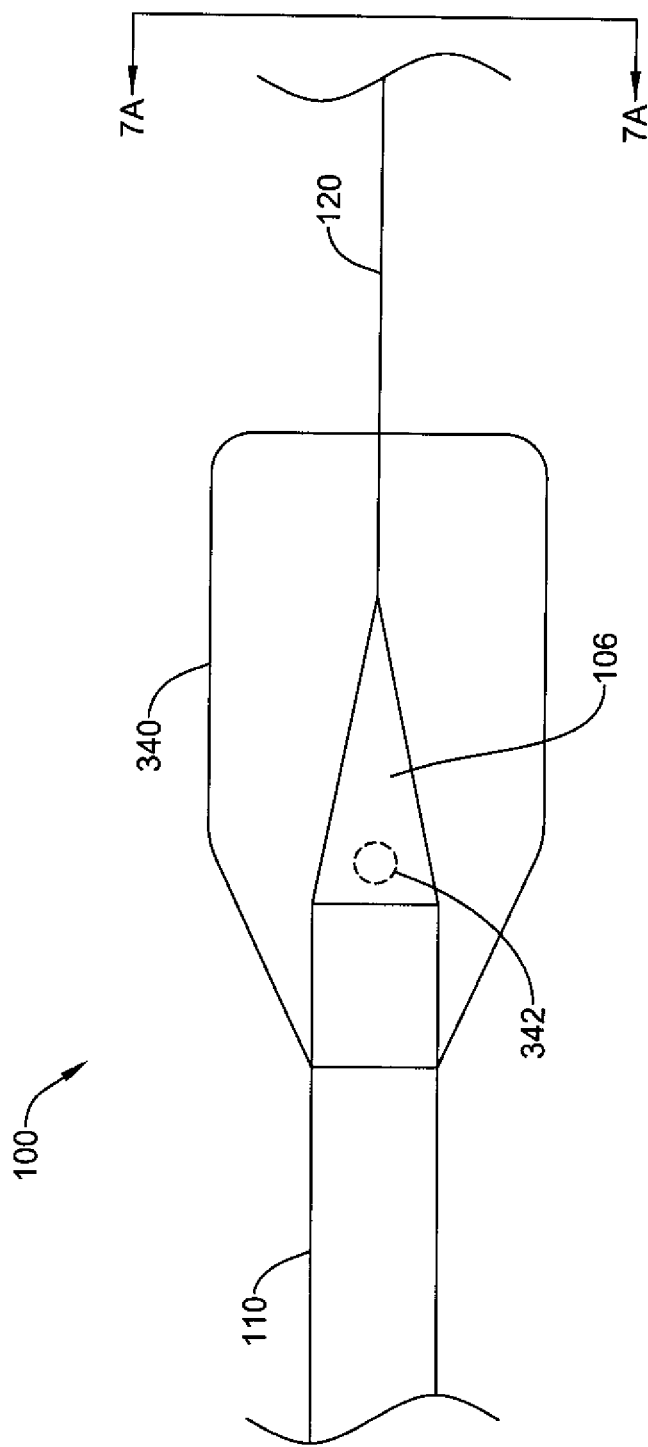
FIG. 7 is a side view of an example guidewire system.

In some embodiments, the expandable protection element 140 may include an inflatable balloon 340, as seen for example in FIGS. 7 and 8, and/or other suitable soft feature. In some embodiments, a suitable soft feature may include an expandable sponge, foam, or soft rubbery material, for example. In some embodiments, in an expanded configuration, the inflatable balloon 340 or other suitable soft feature may include a generally wide, flat cross-section thereby providing a large surface area to contact the wall of the left ventricle 24 and/or the apex 26. In some embodiments, at least a portion of the proximal section 110 of the guidewire 100 may include an inflation lumen extending therethrough to an inflation port 342 opening into the inflatable balloon 340, as may be seen in FIG. 7. In some embodiments, the inflation port 342 may be disposed at or adjacent to a distal end of the proximal section 110. In some embodiments, the inflation port 342 may be disposed within the tapered region 106.

Figure 7A:
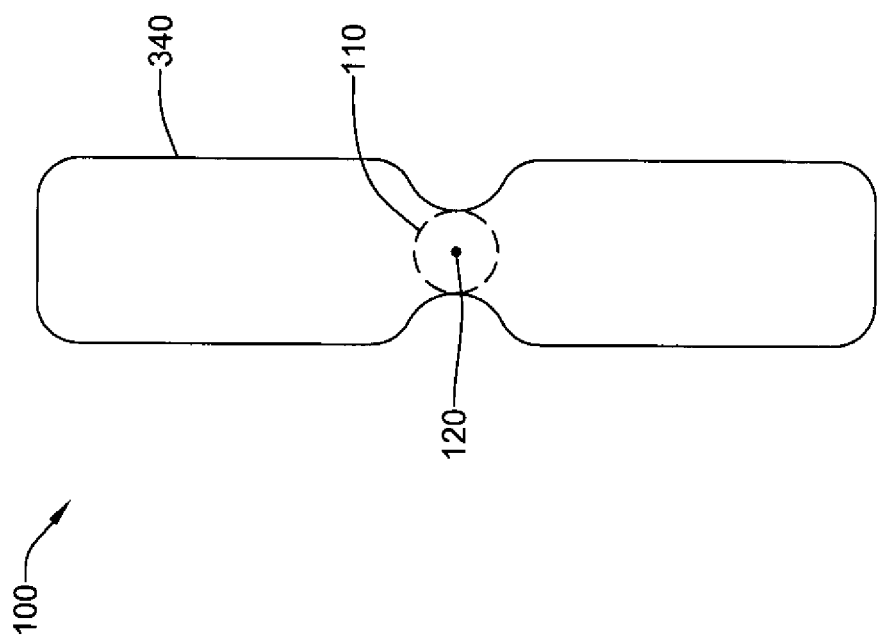
FIG. 7A is an end view of the example guidewire system of FIG. 7.

In some embodiments, the inflatable balloon 340 may include a thin middle section extending along a longitudinal length of the inflatable balloon 340, as seen for example in FIG. 7A, for easier insertion and withdrawal through a guide catheter or delivery system. In some embodiments, the thin middle section may provide enhanced folding characteristics. In some embodiments, a proximal waist of the inflatable balloon 340 may be fixedly attached to the proximal section 110 of the guidewire 100, and a distal waist of the inflatable balloon 340 may be fixedly attached to the distal section 120 of the guidewire 100.

Figure 4:
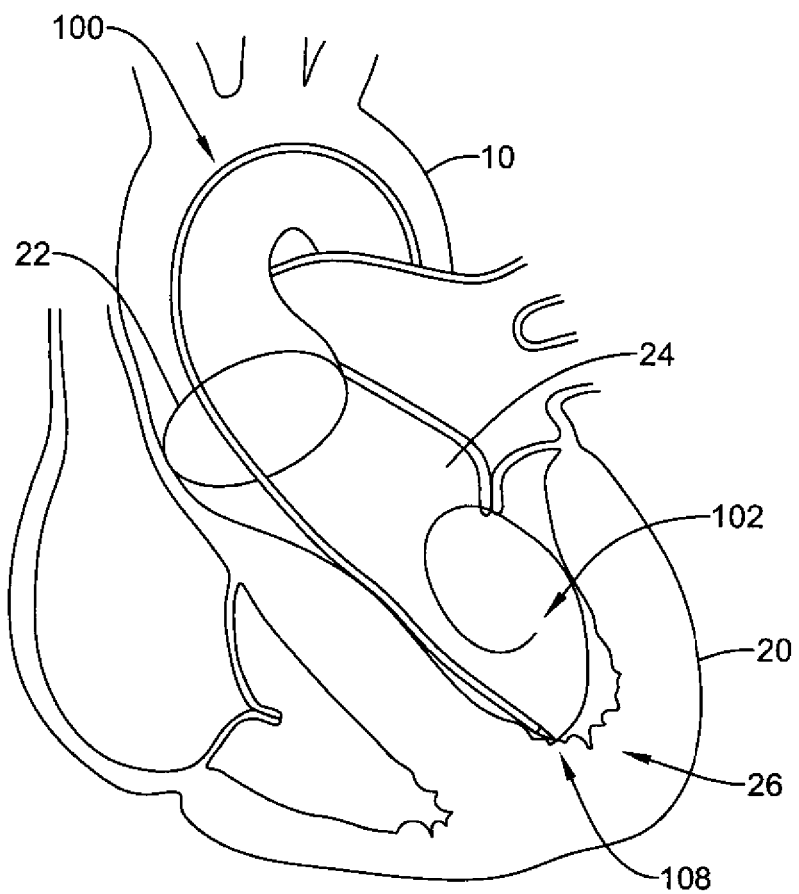
FIG. 4 is a schematic partial view of an aortic heart valve having an example guidewire system disposed therein.

In use, the large surface area of the inflatable balloon 340 may spread force(s) applied to the guidewire 100 out over a larger area of a wall of the left ventricle 24 and prevent a kink 108 from perforating a wall of the left ventricle 24 and/or the apex 26. The skilled artisan will readily recognize that when the guidewire 100 illustrated in FIG. 8 is positioned as shown in FIG. 4, the inflatable balloon 340 or other suitable soft feature may prevent a kink 108 from perforating a wall of the left ventricle 24 and/or the apex 26 by substantially increasing the surface area of the expandable element thereby reducing and/or eliminating puncture pressure (i.e., force per area), and/or protecting any sharp point, tip, or apex along a length of the guidewire 100 that may contact and/or penetrate the adjacent tissue (i.e., the wall of the left ventricle 24 and/or the apex 26). In some embodiments, a shape of the balloon 340 or other suitable soft feature may maintain the guidewire 100 and/or kink 108 in a spaced-apart relationship with the wall of the left ventricle 24, wherein only the inflatable balloon 340 or other suitable soft feature contacts the apex 26.

Figure 9A:
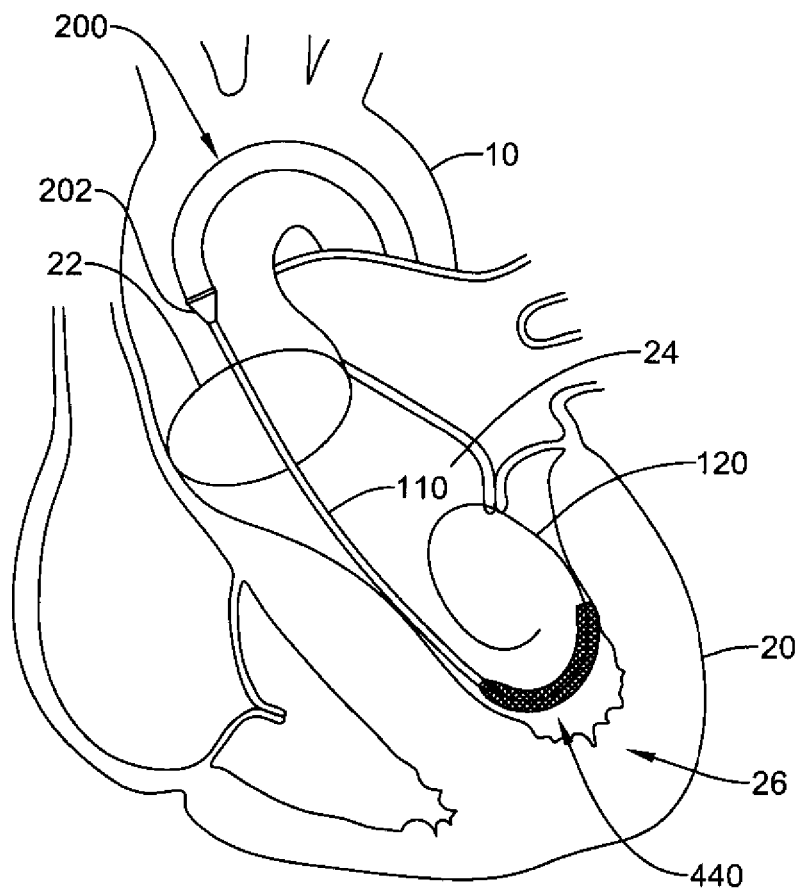
FIG. 9A is a schematic partial view of an example guidewire system disposed within an aortic heart valve.

FIG. 9A schematically illustrates an expandable element 440 fixedly attached to the guidewire 100 at or adjacent to the tapered region 106 in an expanded configuration, and disposed within the left ventricle 24 bridging or extending over the apex 26. In some embodiments, the expandable element 440 may be a stent-like structure, an expandable frame or cage, or other suitable element. In some embodiments, the expandable element 440 may be self-expanding. In some embodiments, the expandable element 440 may be actuated between the collapsed configuration and the expanded configuration by a pull wire, a suture, a release element, or other actuation element.

A proximal end of the expandable element 440 may include a tapered structure extending distally and/or radially outwardly from the proximal section 110 of the guidewire 100. In some embodiments, the expandable element 440 may extend longitudinally along the guidewire 100 and/or the expandable element 440 may maintain the guidewire 100 and/or kink 108 in a spaced-apart relationship with the wall of the left ventricle 24. In some embodiments, only the expandable element 440 contacts the apex 26.

Figure 9B:
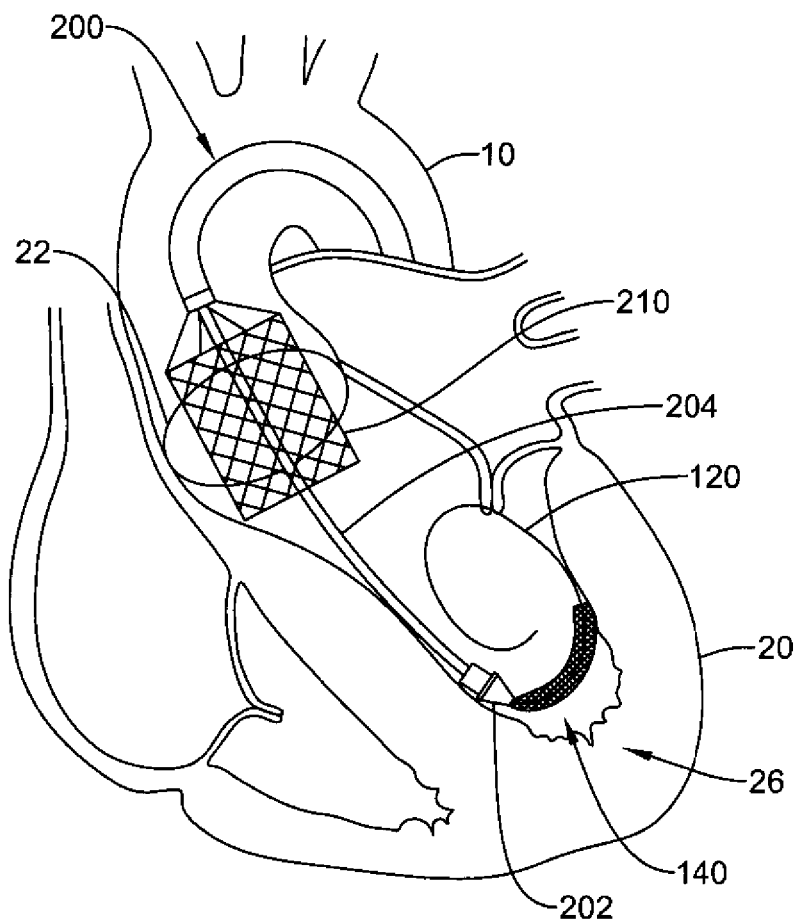
FIG. 9B is a schematic partial view of the example guidewire system of FIG. 9A with an example TAVI device partially advanced thereover.

In use, as a TAVI device 200 is advanced over the guidewire 100, a distal nosecone 202 may engage the proximal end of the expandable element 440. Further advancement of the TAVI device 200 may advance the nosecone 202 and the inner shaft 204 over the expandable element 440, which may gradually collapse toward the collapsed configuration as the nosecone 202 and/or the inner shaft 204 is advanced distally over the expandable element 440, as seen in FIG. 9B.

Figure 10:
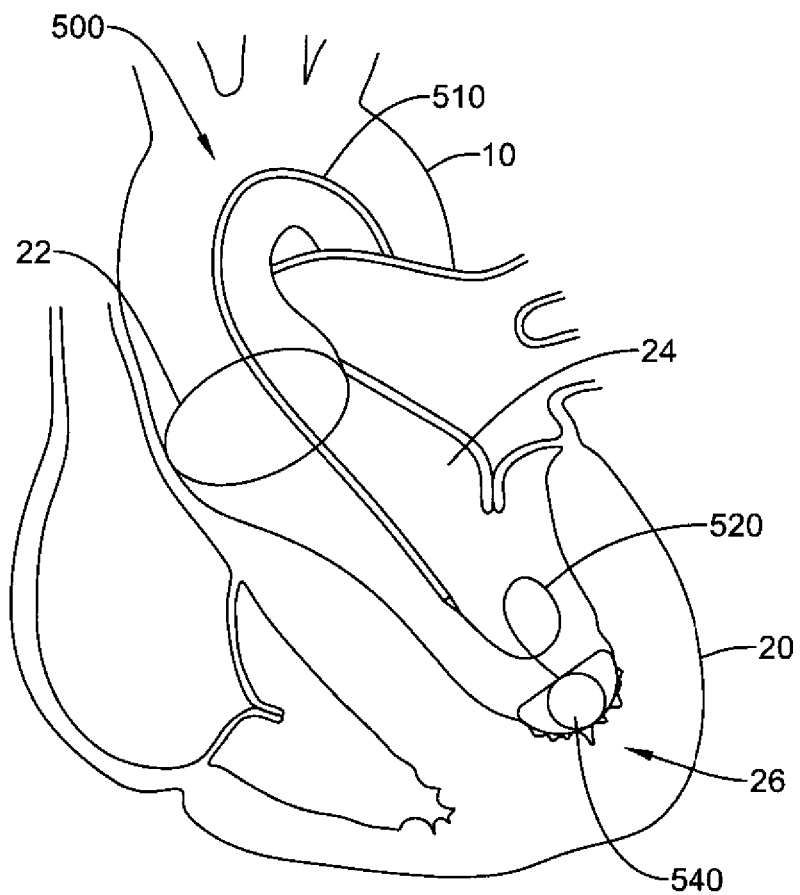
FIG. 10 is a schematic partial view of an example guidewire system.

FIG. 10 schematically illustrates an example guidewire 500 having an expandable element 540 disposed on the guidewire 500 in an expanded configuration, and disposed within the apex 26 of the left ventricle 24. In some embodiments, at least a portion of the guidewire 500 may extend into and/or through the expandable protection element 540. In some embodiments, the expandable element 540 may be disposed at the distal end of the guidewire 500. In some embodiments, the expandable element 540 may include a rounded, irregularly-shaped, and/or ball-shaped balloon or other suitable soft feature. In some embodiments, a suitable soft feature may include an expandable sponge, foam, or soft rubbery material, for example. In some embodiments, in an expanded configuration, the expandable element 540 may include a shape that enables the expandable element 540 to engage and/or interact with the apex 26 such that the distal end of the guidewire may be anchored in the apex 26. In some embodiments, at least a portion of the proximal section 510 and/or the distal section 520 of the guidewire 500 may include an inflation lumen extending therethrough to an inflation port. In some embodiments, the inflation port may be disposed at or adjacent to the distal end of the guidewire 500.

In general, the guidewire 500 may have substantially the same construction and/or characteristics as the guidewire 100 discussed above. In some embodiments, the guidewire 500 may be pre-shaped to generally position the guidewire 500 off of (i.e., in a spaced-apart relationship with) the wall of the left ventricle 24. Such positioning may prevent the nosecone 202 from damaging the wall of the left ventricle 24 and/or from pushing into or damaging the apex 26. Since the guidewire 500 is generally anchored in place suspended within the left ventricle 24, movement of a TAVI device 200 would be prevented from causing the guidewire 500 to perforate the wall of the left ventricle 24.

Figure 11A:
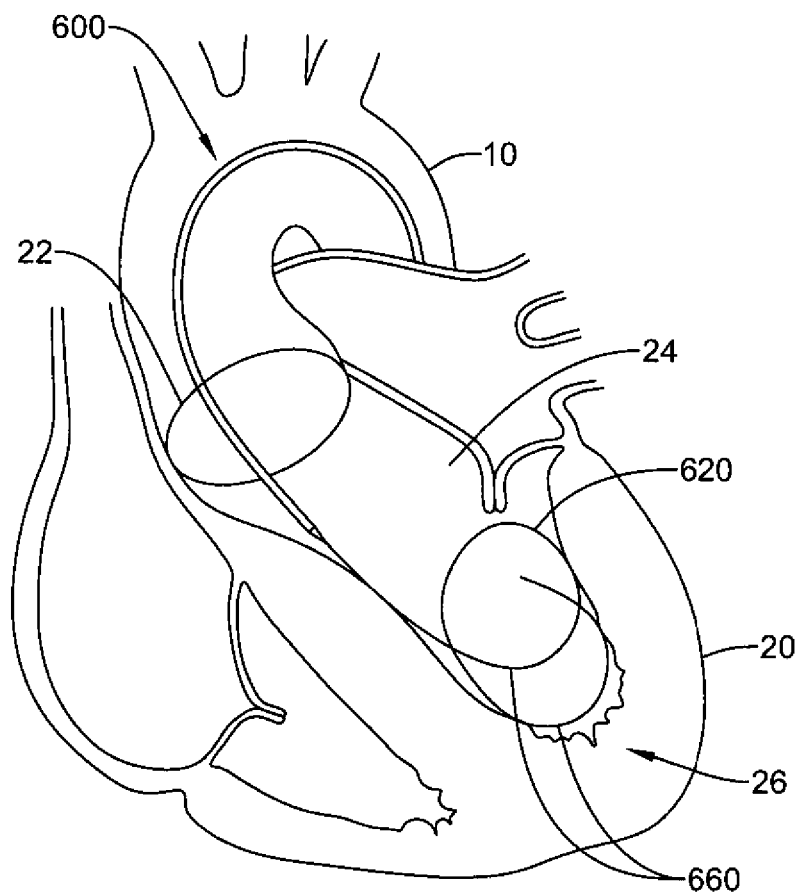
FIG. 11A is a schematic partial view of an example guidewire system.

FIG. 11A schematically illustrates a guidewire 600 disposed within an aorta 10, and/or an aortic valve 22 and a left ventricle 24 of a heart 20. Treatment of an aortic valve 22 using a TAVI device may sometimes involve insertion of a relatively stiff guidewire 600, which may or may not have a relatively flexible distal tip, upstream through the aorta 10 and/or the aortic valve 22 into the left ventricle 24. Later, a suitable TAVI device may be inserted and/or advanced over the guidewire 600 to the heart 20 and/or the aortic valve 22. As shown in FIG. 11A, the guidewire 600 may extend upstream through the aorta 10, across or through the aortic arch, and through the aortic valve 22 into the left ventricle 24 of a patient's heart 20. In some embodiments, a distal end of the guidewire 600 may be positioned within the left ventricle 24 during a TAVI procedure. In general, the guidewire 600 may have substantially the same construction and/or characteristics as the guidewire 100 discussed above.

In use, a distal end of the guidewire 600 may be advanced percutaneously upstream within a patient's aorta 10 to a treatment site (i.e., a patient's heart 20 and/or an aortic valve 22). The distal end may be advanced through the treatment site (i.e., the patient's aortic valve 22) into a patient's left ventricle 24. In some embodiments, the distal section 620 may curl within the left ventricle 24 and/or make contact with an apex 26 of the left ventricle, as seen in FIG. 11A. In general, the distal section 620 may be of sufficient length and flexibility to bend and/or curl within the left ventricle 24 so as to form more than one distal loop. In some embodiments, the distal section 620 of the guidewire 600 may include at least two distal curves 660 traversing the apex 26 and at least one proximal curve disposed therebetween. Each of the distal curves 660 may be in contact with the wall(s) of the left ventricle 24.

By providing additional surface area of the guidewire 100 contacting the wall(s) of the left ventricle (compared to the single loop shown in FIGS. 1, 4, 5A, and 5B, and described above) force(s) applied to the guidewire 600 may be spread out to a greater area of the wall(s) of the left ventricle 24. Additionally, more than one distal loop may increase available counter-traction, thereby making it harder to accidentally pull or remove the guidewire 600 when advancing a TAVI device or other medical device thereover.

Figure 11B:
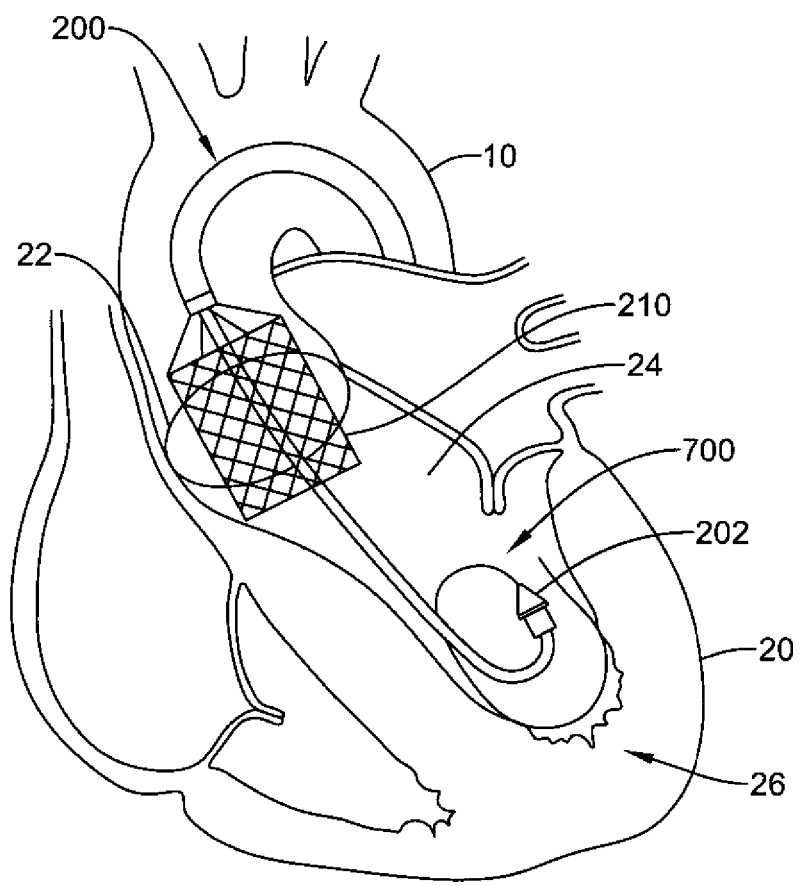
FIG. 11B is a schematic partial view of an example guidewire system with a portion of an example TAVI device disposed thereon.

FIG. 11B schematically illustrates a guidewire 700 disposed within an aorta 10, and/or an aortic valve 22 and a left ventricle 24 of a heart 20. Treatment of an aortic valve 22 using a TAVI device may sometimes involve insertion of a relatively stiff guidewire 700, which may or may not have a relatively flexible distal tip, upstream through the aorta 10 and/or the aortic valve 22 into the left ventricle 24. Later, a suitable TAVI device 200 may be inserted and/or advanced over the guidewire 700 to the heart 20 and/or the aortic valve 22. As shown in FIG. 11B, the guidewire 700 may extend upstream through the aorta 10, across or through the aortic arch, and through the aortic valve 22 into the left ventricle 24 of a patient's heart 20. In some embodiments, a distal end of the guidewire 700 may be positioned within the left ventricle 24 during a TAVI procedure. In general, the guidewire 700 may have substantially the same construction and/or characteristics as the guidewire 100 discussed above.

In use, a distal end of the guidewire 700 may be advanced percutaneously upstream within a patient's aorta 10 to a treatment site (i.e., a patient's heart 20 and/or an aortic valve 22). The distal end may be advanced through the treatment site (i.e., the patient's aortic valve 22) into a patient's left ventricle 24. In some embodiments, the distal section of the guidewire 700 may curl within the left ventricle 24 and/or make contact with an apex 26 of the left ventricle, as seen in FIG. 11B. In general, the distal section of the guidewire 700 may be of sufficient length and flexibility to bend and/or curl within the left ventricle 24 so as to form more than one distal loop. In some embodiments, the distal section of the guidewire 700 may be pre-shaped to generally position at least a portion of the guidewire 700 off of (i.e., in a spaced-apart relationship with) the wall of the left ventricle 24. In some embodiments, a proximally-disposed distal loop, relative to a length of the guidewire 700, may be suspended off of the wall(s) of the left ventricle 24, such that only a more distally-disposed distal loop, relative to the length of the guidewire 700, contacts the wall(s) of the left ventricle 24. Such a configuration may prevent the nosecone 202 from damaging the wall of the left ventricle 24 and/or from pushing into or damaging the apex 26 as the nosecone 202 and/or the TAVI device 200 is advanced distally and/or deployed.

Figure 12A:
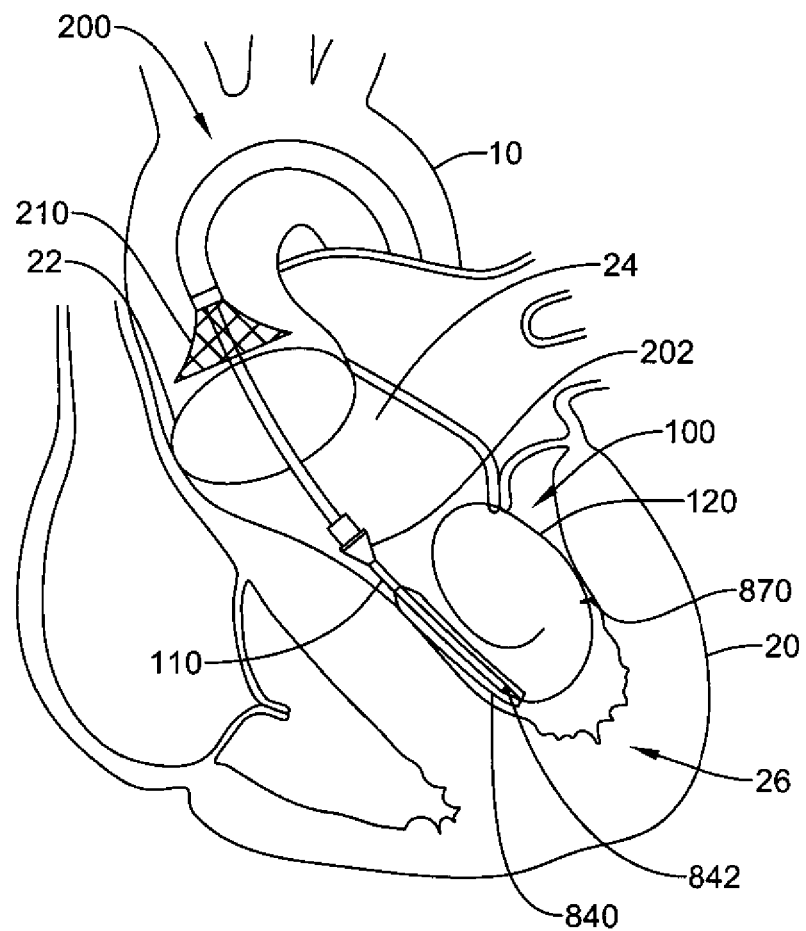
FIG. 12A is a schematic partial view of an example guidewire system with an example TAVI device disposed thereon.

FIG. 12A schematically illustrates an expandable element 840 slidably disposed about an example guidewire 100 in an expanded configuration at a first position. In some embodiments, the expandable element 840 may include an inflatable balloon and/or other suitable soft feature. In some embodiments, a suitable soft feature may include an expandable sponge, foam, or soft rubbery material, for example. In some embodiments, in an expanded configuration, the inflatable balloon or other suitable soft feature may include a generally wide, flat cross-section thereby providing a large surface area to contact the wall of the left ventricle 24 and/or the apex 26. In some embodiments, at least a portion of the proximal section 110 of the guidewire 100 may include an inflation lumen extending therethrough to an inflation port 842. In some embodiments, the inflation port 842 may be disposed at or adjacent to a distal end of the proximal section 110. In some embodiments, the inflation port 842 may be disposed within the tapered region 106.

Figure 12B:
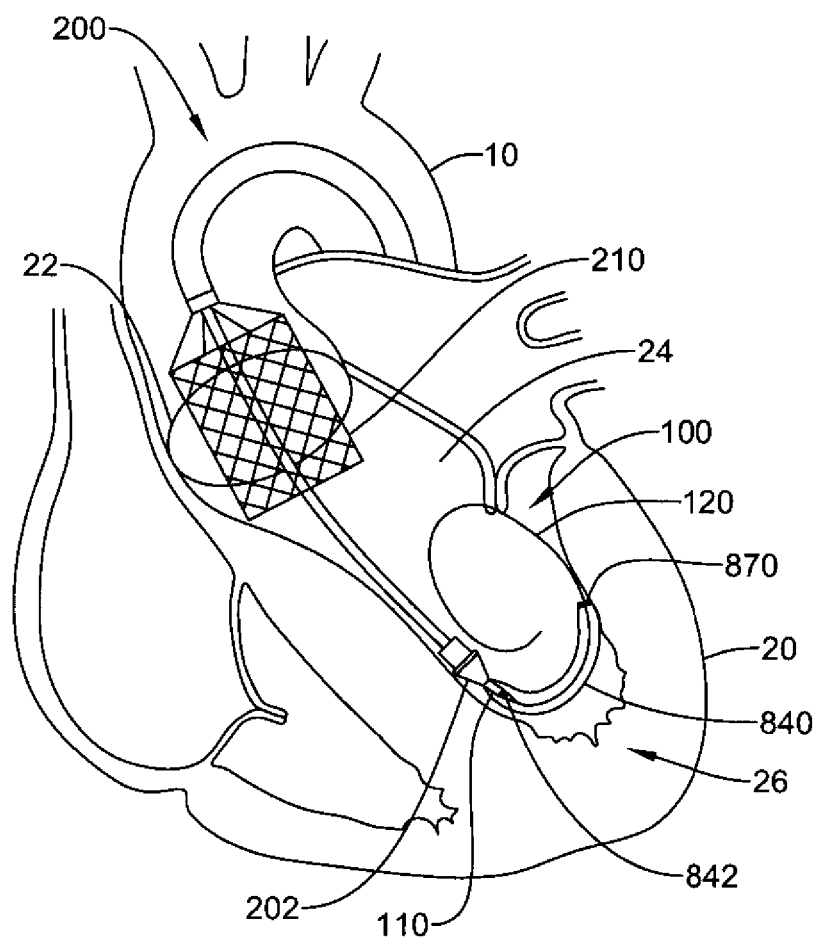
FIG. 12B is a schematic partial view of the example guidewire system of FIG. 12A with an example TAVI device disposed thereon.

In some embodiments, the inflatable balloon may include a thin middle section extending along a longitudinal length of the inflatable balloon for easier insertion and withdrawal through a guide catheter or delivery system. In some embodiments, the thin middle section may provide enhanced folding characteristics. In some embodiments, a proximal waist of the inflatable balloon may be slidably attached to the proximal section 110 of the guidewire 100, and a distal waist of the inflatable balloon may be slidably attached to the distal section 120 of the guidewire 100. Each of the proximal waist and the distal waist may include a sealing feature configured to maintain inflation fluid within an interior of the inflatable balloon while permitting the inflatable balloon to slide axially along the guidewire 100. In some embodiments, a distal stop 870, such as a ring, a protrusion, or other suitable feature, may be disposed on or formed as a part of the distal section 120 of the guidewire 100, wherein the distal stop 870 arrests distal translation of inflatable balloon at a second position, as seen in FIG. 12B. The inflation port 842 may be maintained within an interior of the inflatable balloon (i.e., disposed between the proximal waist and the distal waist) in both the first position and the second position in order to maintain and/or adjust inflation fluid pressure within the inflatable balloon at any time during the procedure.

In use, as a TAVI device 200 and/or a nosecone 202 is advanced distally, the nosecone 202 may come into contact with the expandable element 840. The expandable element 840 may slide axially in a distal direction as the nosecone 202 is advanced until the expandable element contacts the distal stop 870. Once inflated, the large surface area of the inflatable balloon may spread force(s) applied to the guidewire 100 out over a larger area of a wall of the left ventricle 24 and prevent a kink 108 from perforating a wall of the left ventricle 24 and/or the apex 26. The skilled artisan will readily recognize that when the guidewire 100 illustrated in FIG. 12B is positioned as shown in FIG. 4, the inflatable balloon or other suitable soft feature may prevent a kink 108 from perforating a wall of the left ventricle 24 and/or the apex 26 by substantially increasing the surface area of the expandable element thereby reducing and/or eliminating puncture pressure (i.e., force per area), and/or protecting any sharp point, tip, or apex along a length of the guidewire 100 that may contact and/or penetrate the adjacent tissue (i.e., the wall of the left ventricle 24 and/or the apex 26). In some embodiments, a shape of the inflatable balloon or other suitable soft feature may maintain the guidewire 100 and/or kink 108 in a spaced-apart relationship with the wall of the left ventricle 24, wherein only the inflatable balloon or other suitable soft feature contacts the apex 26.

In some embodiments, a method of protecting an apex of a left ventricle of a heart of a patient during a TAVI procedure may include:

inserting a guidewire upstream through an aorta of the patient and into the left ventricle, the guidewire including a relatively stiff proximal section, a relatively flexible distal section joined to the proximal section by a tapered transition region, and an expandable element disposed at a distal end of the guidewire;

positioning the expandable element within the apex;

expanding the expandable element from a collapsed configuration to an expanded configuration within the apex such that the expandable element anchors the distal end of the guidewire;

advancing a TAVI device distally over the guidewire to an aortic valve; and performing a TAVI procedure at the aortic valve.

Additionally, in some embodiments, each of the guidewires described above may include and/or be used with a wire holder configured to fixedly mount the guidewire in place axially during a TAVI procedure. A wire holder may mount using magnetic, mechanical, or other suitable means to an operating or procedure table. A suitable mechanism for securing the guidewire to the wire holder may be used, including but not limited to, friction, mechanical, notching, pinching, extendable feature(s), or other suitable mechanisms. During deployment of the replacement valve member, additional stress and/or force(s) may be applied to the guidewire, which may lead to axial movement and/or damage and/or perforation of the wall of the left ventricle. As such, after advancing the guidewire to the treatment site, a practitioner may engage the guidewire with the wire holder, thereby locking the guidewire in place and preventing axial translation of the guidewire relative to the wire holder.

As such, in some embodiments, a method of protecting an apex of a left ventricle of a heart of a patient during a TAVI procedure may include:

inserting a guidewire upstream through an aorta of the patient and into the left ventricle, the guidewire including a relatively stiff proximal section, a relatively flexible distal section joined to the proximal section by a tapered transition region, and an expandable element disposed about the tapered transition region;

positioning the tapered transition region adjacent the apex;

expanding the expandable element from a collapsed configuration to an expanded configuration within the left ventricle such that the expandable element spans the apex;

advancing a TAVI device distally over the guidewire to an aortic valve; and performing a TAVI procedure at the aortic valve.

In some embodiments, before positioning the tapered transition region adjacent the apex, the distal section of the guidewire may form one or more distal loops within the left ventricle, wherein positioning the tapered region adjacent the apex further includes positioning the one or more distal loops against a wall of the left ventricle.

In some embodiments, one or both of the steps of advancing the TAVI device distally over the guidewire or performing a TAVI procedure may include advancing a nosecone of the TAVI device distally onto the one or more distal loops. In some embodiments, advancing a nosecone of the TAVI device distally may include at least partially collapsing the expandable element as the nosecone is advanced over the expandable element. In some embodiments, advancing a nosecone of the TAVI device distally may translate the expandable element distally along the guidewire until a distal end of the expandable element contacts a distal stop. In some embodiments, distal advancement of the nosecone may be stopped or prevented by the expandable element.

In some embodiments, expanding the expandable element may include releasing a restraining member such that a self-expanding expandable element may be permitted to expand. In some embodiments, expanding the expandable element may include transferring an inflation fluid through an inflation lumen to the expandable element. In some embodiments, expanding the expandable element may include exposing an absorbent sponge or foam to fluid or blood.

In some embodiments, before performing the TAVI procedure, the method may include engaging the guidewire with a guidewire holder disposed external to the patient, the guidewire holder being configured to prevent axial movement of the guidewire during the TAVI procedure.

It should be understood that although the above discussion was focused on a medical device and methods of use within the coronary vascular system of a patient, other embodiments of medical devices or methods in accordance with the invention can be adapted and configured for use in other parts of the anatomy of a patient. For example, devices and methods in accordance with the invention can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the medical devices described herein with respect to percutaneous deployment may be used in other types of surgical procedures as appropriate. For example, in some embodiments, the medical devices may be deployed in a nonpercutaneous procedure, including an open heart procedure. Devices and methods in accordance with the invention can also be adapted and configured for other uses within the anatomy.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

We claim:

1. A method of protecting an apex of a left ventricle of a heart of a patient during a transcatheter aortic valve implantation (TAVI) procedure, the method comprising:
    inserting a guidewire upstream through an aorta of the patient and into the left ventricle, the guidewire including a relatively stiff proximal section, a relatively flexible distal section joined to the relatively stiff proximal section by a transition region, and an expandable element disposed about the transition region;
    advancing the relatively flexible distal section into the left ventricle until a distal curve forms in contact with a left ventricle wall;
    positioning the transition region adjacent the apex;
    expanding the expandable element from a collapsed configuration to an expanded configuration within the left ventricle such that the expandable element spans the apex;
    advancing a TAVI device distally over the guidewire to an aortic valve; and
    performing a TAVI procedure at the aortic valve.

2. The method of claim 1, wherein the relatively flexible distal section is sufficiently flexible to curve within the left ventricle when contact is made with the apex of the left ventricle.

3. The method of claim 1, wherein the relatively flexible distal section is pre-shaped to form a distal loop.

4. The method of claim 3, wherein the relatively flexible distal section forms more than one distal loop.

5. The method of claim 4, wherein a distalmost loop is larger than a more proximal loop.

6. The method of claim 1, wherein the expandable element is an expandable sponge.

7. The method of claim 1, wherein the expandable element is an expandable foam.

8. The method of claim 1, wherein the expandable element is an expandable rubbery material.

9. The method of claim 1, wherein the expandable element is an inflatable balloon.

10. The method of claim 9, wherein the guidewire includes an inflation lumen fluidly connected to the interior of the inflatable balloon.

11. The method of claim 9, wherein the inflatable balloon includes a wide, flat cross-section.

12. The method of claim 9, wherein the inflatable balloon includes a thin middle section extending along a longitudinal length of the inflatable balloon.

13. The method of claim 9, wherein the expanded configuration of the expandable element presents a larger contact area to the apex than a contact area which would be provided by either of the relatively stiff proximal section or the relatively flexible distal section were the relatively stiff proximal section or the relatively flexible distal section to be positioned to span the apex.

14. The method of claim 1, wherein the TAVI device includes a nosecone.

15. The method of claim 14, wherein the TAVI device further includes an inner shaft.

16. The method of claim 14, further comprising a step of advancing the nosecone of the TAVI device distally to least partially collapse the expandable element within the nosecone.

* * * * *